United States Patent
Sun et al.

(10) Patent No.: US 11,104,647 B2
(45) Date of Patent: Aug. 31, 2021

(54) MULTI-FUNCTIONAL, STIMULI-RESPONSIVE MATERIALS, METHODS OF PREPARATION, METHODS OF USE, AND USES THEREOF

(71) Applicant: ADA Foundation, Chicago, IL (US)

(72) Inventors: Jirun Sun, Rockville, MD (US); Nicole Ritzert, Gaithersburg, MD (US); Xiaohong Wang, North Potomac, MD (US)

(73) Assignee: ADA Foundation, Chicago, IL (US)

( * ) Notice: Subject to any disclaimer, the term of this patent is extended or adjusted under 35 U.S.C. 154(b) by 0 days.

(21) Appl. No.: 16/545,110

(22) Filed: Aug. 20, 2019

(65) Prior Publication Data

US 2019/0382343 A1    Dec. 19, 2019

Related U.S. Application Data

(63) Continuation-in-part of application No. 15/723,793, filed on Oct. 3, 2017, now Pat. No. 10,478,488.

(60) Provisional application No. 62/408,826, filed on Oct. 16, 2016.

(51) Int. Cl.
*C07D 213/76* (2006.01)
*G01N 33/543* (2006.01)
*H01B 1/12* (2006.01)

(52) U.S. Cl.
CPC ....... *C07D 213/76* (2013.01); *G01N 33/5438* (2013.01); *H01B 1/128* (2013.01)

(58) Field of Classification Search
None
See application file for complete search history.

(56) References Cited

PUBLICATIONS

Van der Boom et al. "Nanoscale Refractive Index Tuning of Siloxane-BasedSelf-Assembled Electro-Optic Superlattices" Advanced Functional Materials, 2001, vol. 11, No. 5, pp. 393-397.*

* cited by examiner

*Primary Examiner* — Joseph R Kosack

(57) ABSTRACT

A multi-functional, stimuli-responsive material includes a substrate functionalized with a pH-sensitive Azo-QPS compound or co-assemblies containing Azo-QPS compounds. The Azo-QPS compound includes a positively-charged phenyl-azo-pyridinium core, an anion affiliated with the core, a head group, a tail group, a surface bonding group coupling the pH-sensitive Azo-QPS compound to the substrate, and a spacer connecting the pH-sensitive Azo-QPS compound to the surface bonding group.

16 Claims, 12 Drawing Sheets

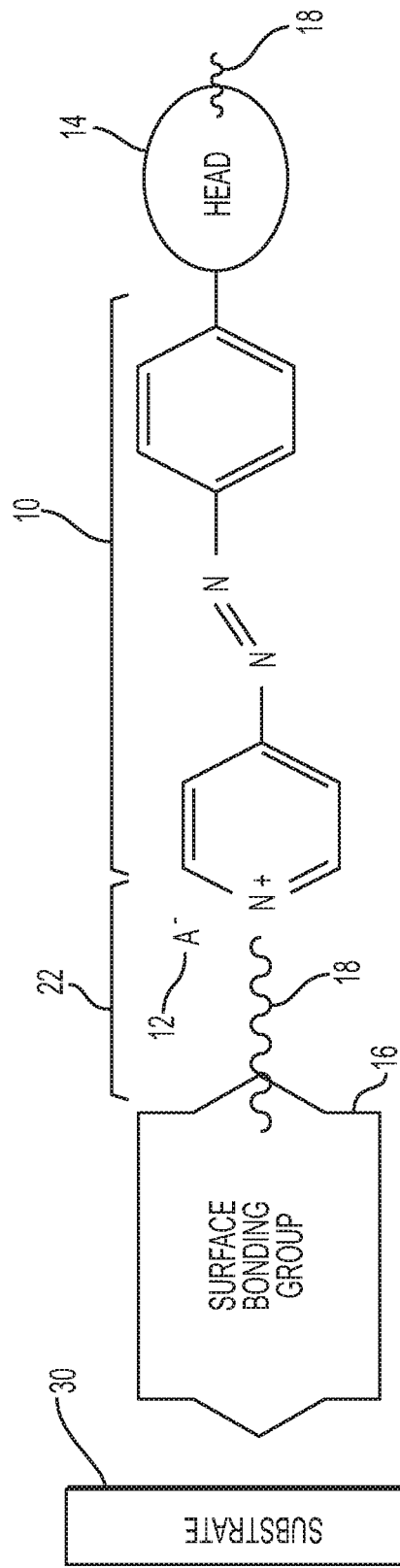
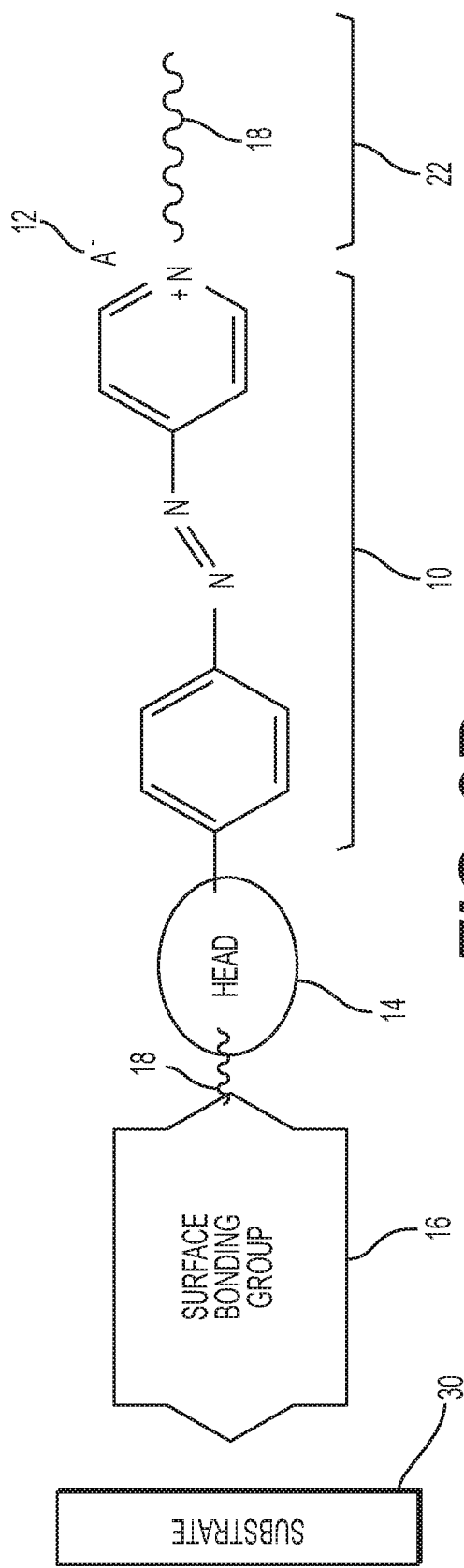

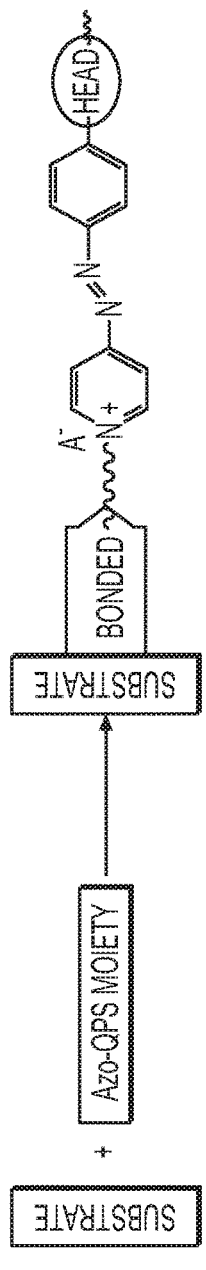
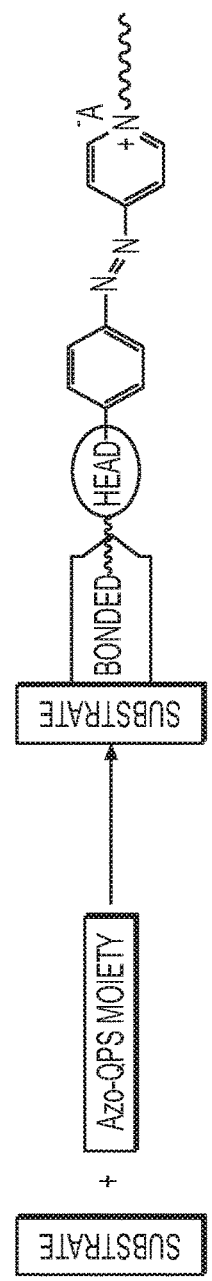
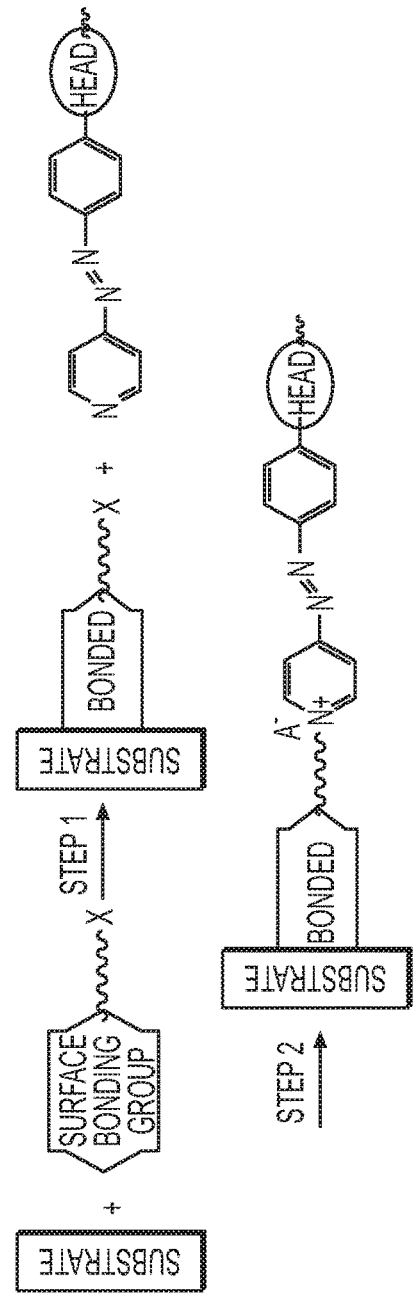
FIG. 4A
FIG. 4B
FIG. 4C

MULTI-FUNCTIONAL, STIMULI-RESPONSIVE MATERIALS, METHODS OF PREPARATION, METHODS OF USE, AND USES THEREOF

RELATED APPLICATIONS

This application is a continuation-in-part of U.S. patent application Ser. No. 15/723,763, filed Oct. 3, 2017, entitled Azo-Quaternary Pyridinium Salts with Acid-Enhanced Antibacterial Efficacy, Methods of Use, Methods of Synthesis, and Uses Thereof, which in turn claims the benefit of U.S. Provisional Patent Application 62/408,826, filed Oct. 16, 2016, entitled Environment Activated Antibacterial Azo-Quaternary Pyridinium Salts, Methods of Use, Methods of Synthesis, and Uses Thereof. The contents of these two patent documents are hereby incorporated by reference.

STATEMENT OF FEDERALLY SPONSORED RESEARCH

The herein disclosed inventions were made with support under NIH/NIDCR #U01DE023752 from the U.S. National Institute of Health (NIH). The U.S. Government may have certain rights to the inventions.

BACKGROUND

Antibiotic resistance, which is the ability of bacteria to resist medication (e.g., antibiotics) so that antibiotics no longer effectively treat infections, can occur when antibiotics are misused, overused, or released into the environment. The World Health Organization states that antibiotic resistance is a current threat to public health. Thus, increasing the efficiency and limiting the use of antibiotics would be beneficial in minimizing antibiotic resistance. As an example, quaternary ammonium salts (QAS) with antimicrobial properties have been developed recently to combat *Streptococcus mutans* (*S. mutans*), the primary causative agent in the formation of dental caries. However, current QAS formulations fail to demonstrate a high effectiveness towards *S. mutans*. Novel synthetic materials with stimuli-induced properties could reduce antimicrobial resistance as well as improve the performance of technologies such as drug delivery, targeted treatments, and biosensors as well as antifouling coatings in biomedical, infrastructure, and food packaging applications.

SUMMARY

A multi-functional, stimuli-responsive material includes a substrate functionalized with a pH-sensitive Azo-QPS compound. The Azo-QPS compound includes a positively-charged phenyl-azo-pyridinium core, an anion affiliated with the core, a head group, a tail group, a surface bonding group coupling the pH-sensitive Azo-QPS compound to the substrate, and a spacer connecting the pH-sensitive Azo-QPS compound to the surface bonding group. The Azo-QPS compounds, besides being pH-sensitive, may be light responsive as well as redox active, meaning the Azo-QPS compounds can undergo reduction and oxidation. The disclosed materials are surface-functionalized substrates and co-assemblies of Azo-QPS compounds with chemically-selected compounds as well as combinations of the substrates and co-assemblies for biosensor, pH indicator, stimuli-responsive delivery, targeted treatment, and antifouling applications. As an example, the herein-disclosed multifunctional Azo-QPS compound may be used for targeted-treatment of acid-producing bacteria in an oral environment. The Azo-QPS compound shows enhanced antibacterial activity at acidic conditions (e.g., pH=5) while in neutral or basic conditions the antibacterial activity is 2 to 50 times lower than in acidic conditions. Such a stimulus-induced antibiotic responds to a proliferation of acid-producing bacteria quicker by "activating" under the acid produced by these bacteria in comparison to the other bacteria. In oral environments, the acid-producing bacteria consume sugar and generate lactic acid. Such metabolic process may cause tooth decay and dental caries. The targeted treatment for caries prevention is achieved by selectively inhibiting the growth of the acid-producing bacteria.

In an embodiment, a multifunctional Azo-QPS with functional groups $R_1$ and $R_2$, has the formula:

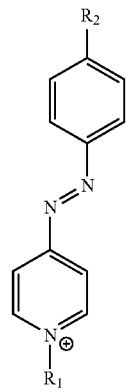

where $R_1$ may be a functional group consisting of —$C_nH_{(2n+1)}$, —$C_nH_{(2n-1)}$, and their derivatives, where n is an integer preferably between 2 and 20. $R_2$ may be chosen from a group consisting of —OH, —$NH_2$, —$NMe_2$, Alkyl, —$OCH_3$, $OC_2H_5$, and their derivatives. $R_2$ also may be chosen from a group consisting of polymerizable functional groups such as methacrylate, acrylate, styrene, vinyl benzyl, and their derivatives. The Azo-QPS compound integrated onto a substrate or into co-assemblies may act 1) as an antibacterial drug towards both Gram-positive and Gram-negative bacteria; 2) as an antibacterial drug with a higher efficacy towards Gram-positive and/or Gram-negative bacteria in acidic environments (pH<6) than in neutral and basic environments; 3) as a pH sensor to determine pH values between 4.1 and 7.9; 4) as a part of immunosensor to quantify an antibody-antigen interaction; 5) as an antibacterial compound that can be integrated into polymeric materials or particles through covalent or non-covalent bonds; 6) as a pH sensor that can be integrated into polymeric materials or particles through covalent or non-covalent bonds; and as anti-fouling materials that can prevent/remove bacteria attachment.

In another embodiment, Azo-QPS compounds consist of six components: 1) a positively charged, pH-sensitive phenyl-azo-pyridinium core (pH-core), 2) an anion (A-) that is affiliated with the pH-core, 3) a head group (Head), 4) a tail group (Tail), 5) an optional surface bonding group that may be chemically bonded onto the substrates, and 6) spacers that connect the pH-core and surface bonding group. The spacers attached to the Head and the nitrogen of the pyridinium in the pH core could be the same or different. The anion is selected from the anions including but not limited to $NO_3^-$, $NO_2^-$, $SCN^-$, $CN^-$, $PO_4^{3-}$, $SO_4^{2-}$, $SO_4^{2-}$, $F^-$, $Cl^-$, $Br^-$, $I^-$, $BF_4^-$, $PF_6^-$, $AsF_6^-$, $SbF_6^-$, $CH_3CO_2^-$, $CF_3SO_3^-$, $(CF_3SO_2)_2N^-$, $(CF_3SO_2)_3C^-$, and $CF_3COO^-$. The Head group is covalently bonded to the pH-core from the phenyl side through C—C or C—O bonding, for example, the C—O bonding in the form of ether or ester functional groups. The "Tail" attached to the nitrogen in the pyridinium of the pH-core consists of a spacer attached to an optional functional group that may be bonded to the substrate through chemical reactions including silanization, polymerization, and thiolation. The spacers in the Head and Tail may be 0 to 16 members of alkyl chain, alkoxyl chain or similar. The surface bonding group may be chemically bonded to the substrate through chemical reactions including but not limited to including polymerization, silanization, and thiolation. An example of the Azo-QPS compound is: (E)-4-((4-(isobutyryloxy)phenyl)diazenyl)-1-(5-(methacryloyloxy)pentyl)pyridinium bromide. The anion, head group, spacer, and surface bonding group are bromide, isobutyloxy, pentyl and methacryl, respectively. The Head is attached to the pH-core through —C—O— bonding. The surface bonding group, methacryl functional group, may be copolymerized through free radical polymerization onto the substrates.

The Azo-QPS compound integrated onto a substrate or into co-assemblies may act 1) as an antibacterial drug towards both Gram-positive and Gram-negative bacteria; 2) as an antibacterial drug with a higher efficacy towards Gram-positive and/or Gram-negative bacteria in acidic environments (pH<6) than in neutral and basic environments; 3) as a pH sensor to determine pH values between 4.1 and 7.9; 4) as a part of immunosensor to quantify an antibody-antigen interaction; 5) as an antibacterial compound that can be integrated into polymeric materials or particles through covalent or non-covalent bonds; and 6) as a pH sensor that can be integrated into polymeric materials or particles through covalent or noncovalent bonds.

DESCRIPTION OF THE DRAWINGS

The detailed description refers to the following figures in which like numerals refer to like items, and in which:

FIGS. 2A and 2B illustrate novel multifunctional Azo-QPS compounds as disclosed herein;

FIGS. 4A-6B illustrate example functionalization methods; and

DETAILED DESCRIPTION

Figure 1:
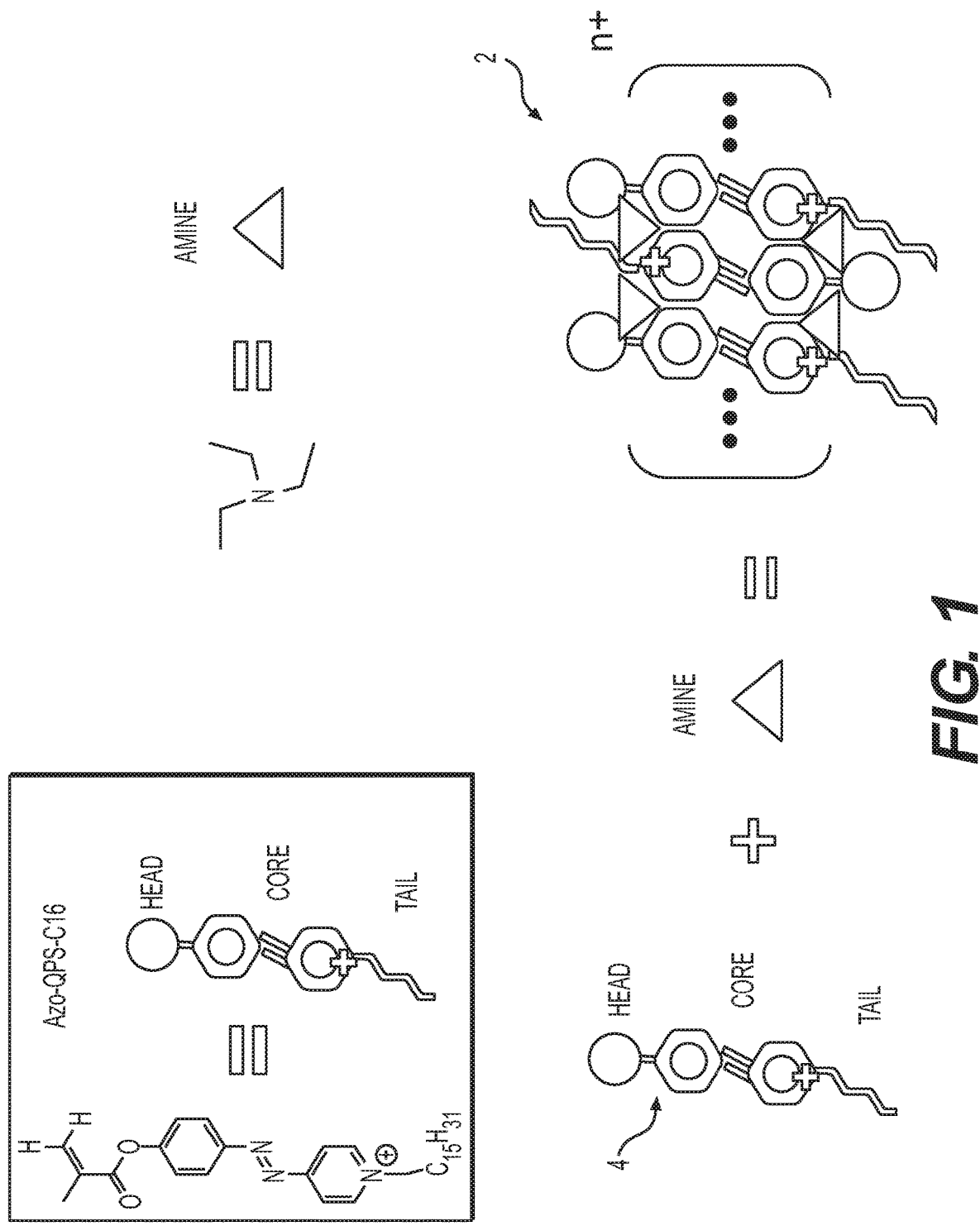
FIG. 1 illustrates and example of co-assembly and disassembly of the herein disclosed novel multifunctional Azo-QPS compounds.

Smart materials with stimuli-induced functionalities are vital in plant and animal survival and reproduction and for applications such as drug delivery, targeted treatment, biosensors, etc. As an example, plants sense approaching herbivores and autonomously release chemicals as repellents or toxins to their natural enemies. Applicants discovered multifunctional azo-quaternary pyridinium salts (Azo-QPS) with acid-induced antimicrobial efficacy for targeted treatment of acid-producing bacteria through selective inhibition of acid-producing bacteria in a multi-species environment. The novel synthetic stimuli-responsive materials may be used in drug delivery, antifouling, and sensors, as well as other biomedical, chemical, and electronic applications. The stimuli include pH, light, chemical, and temperature changes. Applicants further discovered the multi-functional properties of the Azo-QPS compounds may be transformed onto substrates or into co-assembly through novel formulation of Azo-QPS and functionalization of the substrates.

These compounds comprise, generally, combined azo functional groups with phenyl and quaternary pyridinium salt functional groups. An example structural formula for an Azo-QPS compound is shown below:

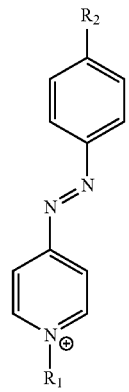

In this formulation, $R_1$ is a functional group consisting of —$C_nH_{(2n+1)}$, —$C_nH_{(2n-1)}$, and their derivatives, where n is an integer between 2 and 20, and $R_2$ is chosen from a group consisting of —OH, —$NH_2$, —$NMe_2$, —$C_nH_{(2n+1)}$, —$C_nH_{(2n-1)}$, —$OCH_3$, $OC_2H_5$, and their derivatives. $R_2$ also may be chosen from a group consisting of polymerizable functional groups such as methacrylate, acrylate, styrene, vinyl benzyl, and their derivatives.

FIGS. 2A and 2B disclose embodiments of multifunctional Azo-QPS compounds designed to be attached to a substrate or to form co-assemblies with other Azo-QPS compounds or other chemical compounds. Similar to the embodiment in the previous paragraph, these Azo-QPS compounds include a positively charged, pH-sensitive phenyl-azo-pyridinium core (pH-core) 10, an anion ($A^-$) 12 affiliated with the pH-core 10, a head group (Head) 14, a tail group (Tail) 22, and a surface bonding group 16 that may be covalently bonded onto substrates 30, and spacers (∿∿∿) 18 that connect the nitrogen of the pyridinium ring in pH-core 10 and the surface bonding group 16 or connect the Head 14 and the surface bonding group 16. The spacers 18 may be 0 to 16 members of alkyl chain, alkoxyl chain or similar and may be the same or different for the Head 14 and Tail 22. The Head 14 is covalently bonded to the pH-core 10 from the phenyl side through C—C or C—O bonding, for example, the C—O bonding in the form of ether or ester functional groups. The Tail 22 is attached to the nitrogen in the pyridinium of the pH-core 10 and consists of a spacer 18 attached to an optional surface bonding group. The surface bonding group 16 may be chemically bonded to the substrate 30 through chemical reactions including but not limited to polymerization, silanization, and thiolation. The anion 12 is selected from anions including but not limited to $NO_3^-$, $NO_2^-$, $SCN^-$, $CN^-$, $PO_4^{3-}$, $SO_4^{2-}$, $SO_4^{2-}$, $F^-$, $Cl^-$, $Br^-$, $I^-$, $BF_4^-$, $PF_6^-$, $AsF_6^-$, $SbF_6^-$, $CH_3CO_2^-$, $CF_3SO_3^-$, $(CF_3SO_2)_2N^-$, $(CF_3SO_2)_3C^-$, and $CF_3COO^-$. An example of the Azo-QPS compound is (E)-4-((4-(isobutyryloxy)phenyl)diazenyl)-1-(5-(methacryloyloxy)pentyl)pyridinium bromide. In this compound, the anion 12, Head 14, spacer 18, and surface bonding group 16 are bromide, isobutyloxy, pentyl, and methacryl, respectively. The Head 14 is attached to the pH-core 10 through —C—O— bonding.

The substrates 30 may comprise conductive materials including conductors or semiconductors: carbon (e.g., glassy carbon, graphite, amorphous carbon), metal (e.g., gold, platinum and silver), silicon, metal oxide (e.g., indium tin oxide (ITO), tin oxide), and conductive organic polymers (e.g., polyaniline, polypyrrole, poly(vinylferrocene)). The substrates 30 also may comprise nonconductive (i.e., insulating) materials such as polymers (e.g., polyester, vinyl ester resin), glass, silicon oxide.

The substrates 30 include the above materials in the form of films, particles, nanoparticles, particles with porous structures, mesoporous particles, and membranes in any combination of material size and form (e.g., gold nanoparticles on a glass microscope slide, 100 nm-thick polythiophene film on 125 μm-thick polyimide film).

The multifunctional Azo-QPS compounds are stimuli-responsive, meaning the compounds alter their properties and effects in an environmental setting depending on the physical or chemical characteristics of that environment. For example, one of the herein disclosed Azo-QPS compounds provides pH-sensitive antibacterial properties that selectively inhibit the growth of acid-producing bacteria in a multi-species environment.

Because the Azo-QPS compounds are stimuli-responsive, the compounds may be employed to provide in situ targeted treatment to bacterial infections that promises an effective approach against antibacterial resistance. In one aspect, the Azo-QPS compounds regulate antibacterial efficacy in biologically relevant conditions by sensing pH changes in the local environment and, in response, undergoing a reversible disassembly process that controls the number of active antimicrobial sites thereby boosting antibacterial activity. FIG. 1 illustrates an example reversible co-assembly/disassembly process. As can be seen in FIG. 1, assembled Azo-QPS molecules and base-moieties 2 disassemble as pH decreases from slightly basic pH (pH 8) to an acidic pH (pH 4). At the acidic pH, more disassembled Azo-QPS molecules 4 are and thus able to generate more antimicrobial sites. Characterization of this reversible pH-dependent assembly/disassembly is discussed in detail herein in Examples 12 and 14. Also disclosed herein in more detail, applicants discovered that such pH-regulating antibacterial activity, based on minimum bactericidal concentrations (MBC), is 16-times more effective on *Escherichia coli* (*E. coli*) and 8-times more effective on *Streptococcus mutans* at pH 4.1 as compared to pH 7.9.

The design, synthesis, and characterization of these multifunctional Azo-QPS compounds are disclosed herein in detail. Also disclosed are the formulations' pH-sensitive physicochemical properties as evaluated by UV-Vis spectroscopy, dynamic light scattering, and electrochemical methods. Further disclosed are delivery mechanisms for the acid-induced, pH-controlled antibacterial activity. Finally, disclosed are applications for the multifunctional Azo-QPS compounds.

Applicants hypothesized that the herein disclosed Azo-QPS compounds would show a high activity only at acidic conditions (e.g., pH=5) and that in neutral or basic conditions, the new Azo-QPS compounds would exhibit a much lower level (2-50 times lower) antibacterial activity. With these predicted characteristics, such "stimulus-induced" antibiotics (i.e., the new Azo-QPS formulations are "activated" only when the environmental pH becomes acidic, which, as noted above, indicates the accumulation of *S. mutans* and the initiation of tooth decay) can help reduce or prevent the build-up of potent antibacterial agents in the oral environment and thereby lessen the development of antibacterial resistance.

In particular, applicants developed and characterized a family of Azo-QPS compounds. Applicants then evaluated the antibacterial activity of these Azo-QPS compounds towards Gram-positive *E. coli* and Gram-negative *S. mutans* bacteria. Applicants discovered that the antibacterial efficacy of the herein disclosed Azo-QPS compounds is highly sensitive to changes within physiological pH ranges as a result of reversible assembly (see FIG. 1) that can be controlled by pH-changes. Applicants further discovered that the reversible assembly can be controlled by redox reagents. The above-illustrated Azo-QPS formulation may exhibit acid-induced, pH-controlled reversible switching of antibacterial activity across a broad-spectrum of bacteria. This QPS, referred to herein as Azo-QPS-C16, contains a sixteen-carbon chain tail and an azobenzene derivative that detects pH changes and adjusts the physicochemical properties of the Azo-QPS-C16 accordingly in a physiological pH range from pH about 4.0 to 8.0. In an infection scenario, the antibacterial efficacy of Azo-QPS-C16 may be triggered locally by acidic metabolic products of nearby bacteria to subsequently kill the bacteria, eliminating the need for external means of intervention. For example, *S. mutans* and their biofilms consume sugars and generate acids, presenting a significant threat to tissue health and biomedical devices including orthopedic implants and dental restorations. Thus, Azo-QPS-C16 may attack bacteria in response to the bacteria's own metabolic activity. Consequently, Azo-QPS-C16 may prevent and/or treat tissue infections and may protect biomedical devices from bacteria-related failure. This function of Azo-QPS-C16 in medical devices is similar to that of natural short cationic amphiphilic peptides that serve as both antibiotics and innate immune modulators in nearly every form of life. Successful application of Azo-QPS-C16 avoids chronic use of active antimicrobials and thus reduce environmental accumulation of antibiotics.

An embodiment of the herein disclosed new Azo-QPS compound was designed with a readily polymerizable methacrylate $R_2$ group; this Azo-QPS compound exhibits high antibacterial effectiveness towards Gram-positive *E. coli* and Gram-negative *S. mutans* bacteria. Similarly, when the $R_2$ group is acrylate, styrene, or vinyl benzyl, the corresponding Azo-QPS compound also should exhibit high antibacterial effectiveness towards Gram-positive (*E. coli*) and Gram-negative (*S. mutans*) bacteria and thus would be a candidate for readily producing antibacterial materials. In addition, the effectiveness of the new Azo-QPS formulations is sensitive to a varying environmental pH. Specifically, at lower pH (pH=4) conditions, the Azo-QPS formulations show much higher (2-50 times) antibacterial activity than at higher pH levels (pH=7-9, for example). Such disparity in antibacterial activity is due to the reversible assembly of Azo-QPS; the reversible assembly can be induced chemically (e.g., by triethylamine ($NEt_3$) and acetic acid ($CH_3COOH$)) or by switching pH of the environment. This discovery shows great potential in renovating current bacterial drugs as the new Azo-QPS formulations to help prevent the build-up of antibiotics, which in turn may serve as a solution to a universal problem of bacterial resistance to antibiotics.

In addition, the Azo-QPS compounds may serve as multifunctional components of immunosensors that not only have antibacterial properties but also respond to reduction or oxidation (i.e., redox) reactions or antigen-antibody reactions. These applications could be used to quantify the concentration of antigens in media such as saliva, blood, or aqueous solutions.

Other possible uses for the Azo-QPS formulations include:

- Acting as an antibacterial drug with high efficacy (low µg/mL level) towards Gram-positive (*E. coli*) and Gram-negative (*S. mutans*) bacteria.
- Acting as an antibacterial compound that can be integrated into polymeric materials. The vinyl functional group can act as the linker, and applicants have shown that methacrylate functional groups may be included without interfering or compromising the potent antibacterial activity of Azo-QPS.
- Acting as polymeric Azo-QPS materials in dental composites, other medical devices, biomaterials, and food-packaging materials, for example.
- Acting as a sensor. The high sensitivity of Azo-QPS to both physiological pH levels and redox potentials makes it possible for Azo-QPS to function as an immunosensor and a pH sensor.
- Acting as anti-fouling materials. The stimuli-responsive physical and chemical properties of Azo-QPS compounds enable the switch of wettability and protein adsorption on the functionalized substrates through changing co-assembly/disassembly in responding to the chemical and physical changes in the environments. The dynamic changes in wettability and protein adsorption prevent/remove bacteria attachment onto the substrates.

These and other applications and uses of the novel multifunctional Azo-QPS compounds are described herein in detail.

EXAMPLES 1-12: SYNTHESIS AND FUNCTIONALIZATION

Example 1: Synthesis of (E)-1-hexadecyl-4-((4-(methacryloyloxy)phenyl) diazenyl)-pyridinium bromide (Named Azo-QPS-C16)

Figure 3:
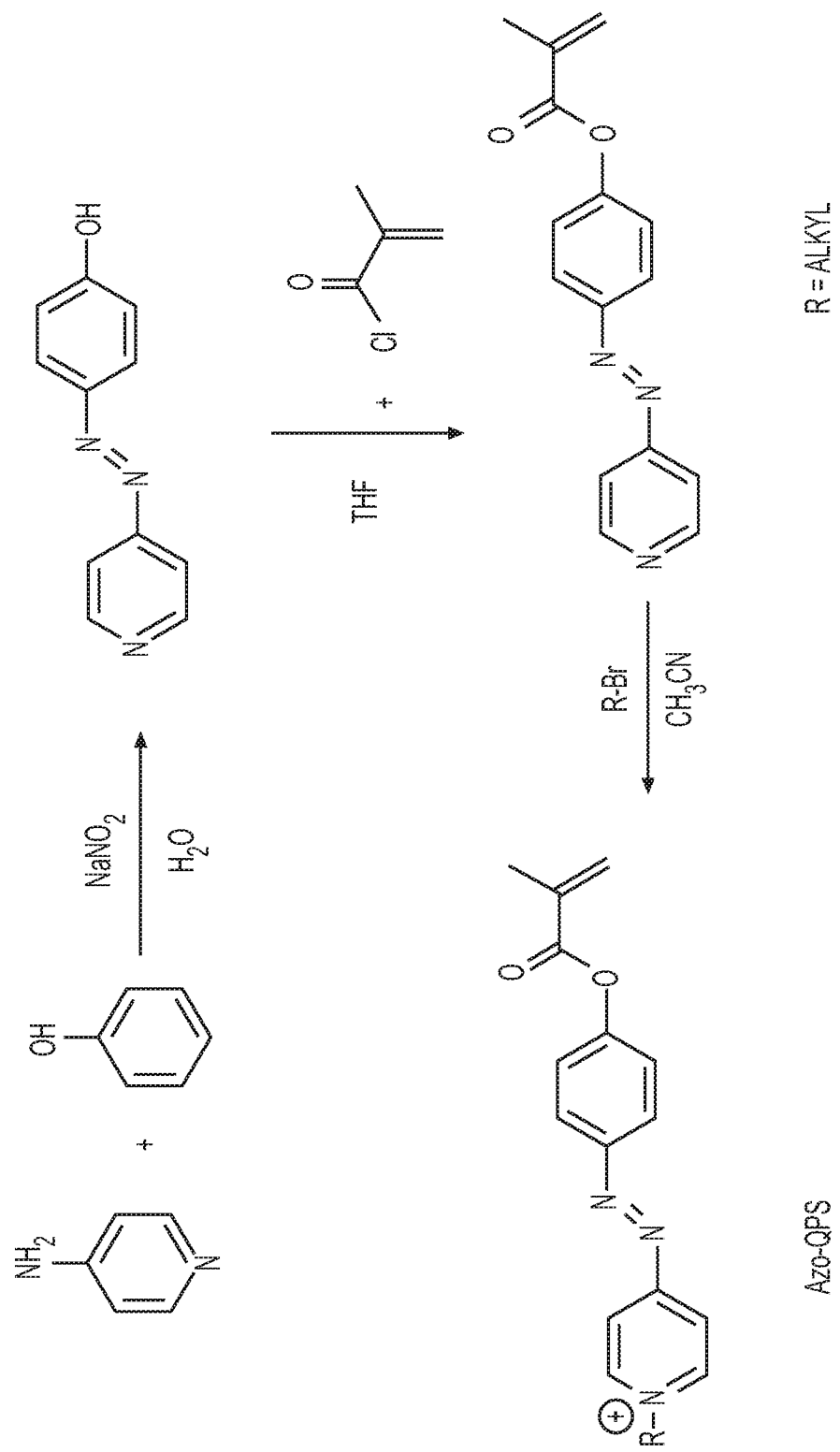
FIG. 3 illustrates an example synthesis of a herein disclosed novel small organic compound, Azo-QPS-C16.

FIG. 3 illustrates an example synthesis of Azo-QPS-C16. The compound was synthesized in three steps starting from 4-aminopyridine and phenol. First, a 4-(4-hydroxyphenylazo) pyridine core was obtained through an azo coupling reaction. Second, the core was functionalized by methacryloyl chloride to equip a polymerizable head group onto the phenyl ring. This head group may be copolymerized with other C=C functional groups, thus enabling the final molecule to be anchored onto polymers and filler particles. Third, a sixteen-carbon tail was attached to the pyridine ring through refluxing with 1-bromohexadecane. The desired product, Azo-QPS-C16, was obtained as a red powder in 49% overall yield.

General Information for Synthesis and Characterization.

Commercially available materials purchased from Alfa Aesar (Tewksbury, Mass., USA), Sigma-Aldrich (Saint Louis, Mo., USA) and TCI America (Portland, Oreg., USA) were used as received. Proton and carbon nuclear magnetic resonance (1H and 13C NMR) spectra were recorded on a Bruker instrument (600 MHz, Billerica, Mass., USA) using 5 mm tubes. Chemical shifts were recorded in parts per million (ppm, δ) relative to tetramethylsilane (δ=0.00), dimethylsulfoxide (δ=2.50) or chloroform (δ=7.26). 1H NMR splitting patterns are designated as singlet (s), doublet (d), triplet (t), quartet (q), dd (doublet of doublets), and m (multiplets). High-resolution mass spectra (MS) were recorded on a JEOL AccuTOF (Peabody, Mass., USA) for ESI-TOF-MS analysis.

Five (5) g (53.2 mmol) of phenol and 4 g (60 mmol) of sodium nitrite were dissolved in 20 mL 10% (w.t.) sodium hydroxide aqueous solution, and the mixture was stirred in an ice-bath at 0-4° C. The mixture was added dropwise to a pre-cooled solution made from 6 g (63.8 mmol) of 4-aminopyridine in a hydrogen chloride aqueous solution. The reaction was stirred in the ice-bath for 30 minutes, and then stirred at room temperature overnight. The pH of the reaction was adjusted to 6-7 with ten percent by weight (10% (w.t.)) sodium hydroxide; the precipitation was collected by filtration, and dried in air. The azo product was used in the next step without further purification.

In a next step, 4 g (20.1 mmol) of the azo and 1.25 equivalent of trimethylamine was dissolved in tetrahydrofuran (THF). One (1) equivalent of methacryloyl chloride was added to the reaction dropwise. The reaction was stirred at room temperature for 2 hours. The Azo-QPS-methacrylate compound was purified by column chromatography with an 87% yield.

Finally, the Azo-QPS-methacrylate compound was refluxed with 1.5 equivalent of desired alkyl bromide in acetonitrile for three days. The resulting dark red product was further purified by recrystallization with ether and acetone, affording 48-56% yield of Azo-QPS-C16. Chemical shift of protons in 1H NMR (600 MHz, CDCl3) spectrum follows: δ 9.64 (d, J=6.0 Hz, 2H), 8.30 (d, J=6.0 Hz, 2H), 8.10 (d, J=6.0, 11.0 Hz, 2H), 7.40 (d, J=16.0, 2H), 6.42 (s, 1H), 5.86 (s, 1H), 5.11 (t, J=7.4 Hz, 2H), 2.08 (m, 5H), 1.33 (m, 26H), 0.88 (m, 3H) ppm; 13C NMR (600 MHz, CDCl3) δ 165.01, 160.42, 156.39, 149.86, 147.21, 135.34, 128.44, 126.27, 123.07, 120.50, 62.03, 32.11, 31.93, 31.17, 29.70, 29.69, 29.66, 29.64, 29.60, 29.51, 29.37, 29.10, 28.77, 26.15, 22.70, 18.32, 14.12 ppm. Hi-Res MS (ESI): m/z calcd. for C31H46N3O2+, 492.3585; found [M]+: C31H46N3O2+, 492.3599.

Examples 2-12: Functionalization Techniques

As used herein, functionalization refers to changing the surface of a substrate by physical absorption of or chemical treatment with Azo-QPS compound, producing Azo-QPS derivatives on the substrate. The process of physical absorption or chemical treatment are defined as functionalization, and the Azo-QPS containing substrates are defined as functionalized substrates.

Example 2: Surface Adsorption

A first example of functionalization is adsorbing layer(s) of the Azo-QPS-C16 compound on the surface of glassy carbon electrodes through intermolecular forces. Here, the glassy carbon electrode is the substrate 30. The Azo-QPS compound is dissolved in dimethyl sulfoxide (DMSO) or isopropanol at a concentration of 1 mmol/L (572 µg/mL) and then diluted with phosphate buffer, DMSO, or isopropanol to a final concentration of 0.1 mmol/mL 0.34 mmol/L, or 0.65 mmol/L. The Azo-QPS compound is first dissolved in DMSO or isopropanol due to the compound's limited solubility in water. The glassy carbon electrode is immersed in the solution for a given amount of time, typically 30 to 60 minutes, and then rinsed with water to remove any Azo-QPS compound not adsorbed to the glassy carbon surface. The applicants propose that Azo-QPS-C16 can be adsorbed on other substrates such glass slides by replacing the glassy carbon with the other surface or by using methods based on surface tension, e.g., Langmuir-Blodgett films.

Examples 3-6: Single Molecular Layer Functionalization

Additional functionalization examples include single molecular layer functionalization in which the Azo-QPS compound was covalently bonded to a substrate 30 as a single molecular layer through reactions including silanization and thiolation. FIGS. 4A-4C illustrate examples using approaches, referred to herein as one-step attachment (FIGS. 4B and 4B) and two-step attachment (FIG. 4C), to complete the attachment.

In one example, Azo-QPS compound was attached to a glassy carbon electrode substrate using silanization and a two-step attachment (FIG. 4C) in which the surface bonding group was 3-bromopropyltrimethoxysilane (BPTMS) or 7-bromoheptyltrimethoxysilane (BHTMS) and the Azo-QPS compound was (4-(methacryloyloxy)phenyl) diazenyl)-pyridine (Azo-QPS-CO). The glassy carbon was polished with 1 μm alumina and sonicated in water for 5 minutes. After rinsing with water, the glassy carbon was immersed in 0.1 mol/L $H_2SO_4$. Then, the electrochemical potential of the glassy carbon was swept between +1.50 V and 0.00 V vs. Ag|AgCl|1 mol/L KCl at 50 mV/s for 10 cycles to make hydroxyl functional groups on the glassy carbon substrate. This step is necessary so that the BPTMS or BHTMS can covalently bond with the hydroxyl groups. After rinsing with water in drying in air 50 to 60 minutes, a solution containing 2% (v/v) BPTMS or BHTMS with 0.1% (w/w) formic acid in acetone was brushed on the surface of the glassy carbon. The brushing step was repeated two times, waiting 5 min between each step. The glassy carbon with BPTMS or BHTMS was dried overnight (about 16 hours) at room temperature. Then, the glassy carbon was rinsed with isopropanol and dried in desiccator at room temperature RT at least 24 hours to complete the reaction between the silane and the glassy carbon substrate. The glassy carbon was then immersed in 2 mmol/L (114 μg/mL) Azo-QPS-CO in acetonitrile at 50° C. for 8 hours, cooled to room temperature overnight (about 16 hours), and rinsed with isopropanol.

Example 3

In a one-step attachment example, the Azo-QPS compounds were attached to a substrate as one unit. FIG. 4A illustrates example 3, a one-step attachment from the pyridinium (Tail) side of the Azo-QPS compound.

Example 4

FIG. 4B illustrates example 4, a one-step attachment from the Head side of the Azo-QPS compound.

Examples 5-6: Two-Step Attachment

In a two-step attachment, an embodiment of which is shown in FIG. 4C, the substrate was functionalized first by attaching the surface bonding group and a spacer. The spacer contained a functional group (X) that in a second step reacted with the pyridine of the pH-core to form a quaternary pyridinium salt: when X was a halide, a quaternary pyridinium salt was produced through a Menshutkin reaction; when X was —OH, a quaternary pyridinium salt was produced through a Mitsunobu reaction.

Example 5: Two-Step Attachment Using Silanization

A glass slide was first silanized by [11-(2-bromo-2-methyl)propionyloxy]undecyltrichlorosilane (BMPTCS-11). The products then underwent a Menshutkin reaction to yield the pyridinium salt attached on the glass slide.

Example 6: Two-Step Attachment Using Thiolation

A gold substrate was first thiolated using 6-mercapto-1-hexanol. The product then underwent Mitsunobu reaction to yield Azo-QPS on the gold substrate.

Examples 7-10: Surface Functionalization with Polymerization

A third functionalization technique involved surface functionalization with polymerization: the surface functionalization with polymerization was achieved by grafting polymers on the substrate or by copolymerization. Two-step and three-step grafting approaches were used for grafting polymers onto a substrate.

Examples 7-8: Two-Step Grafting

Figure 5A:
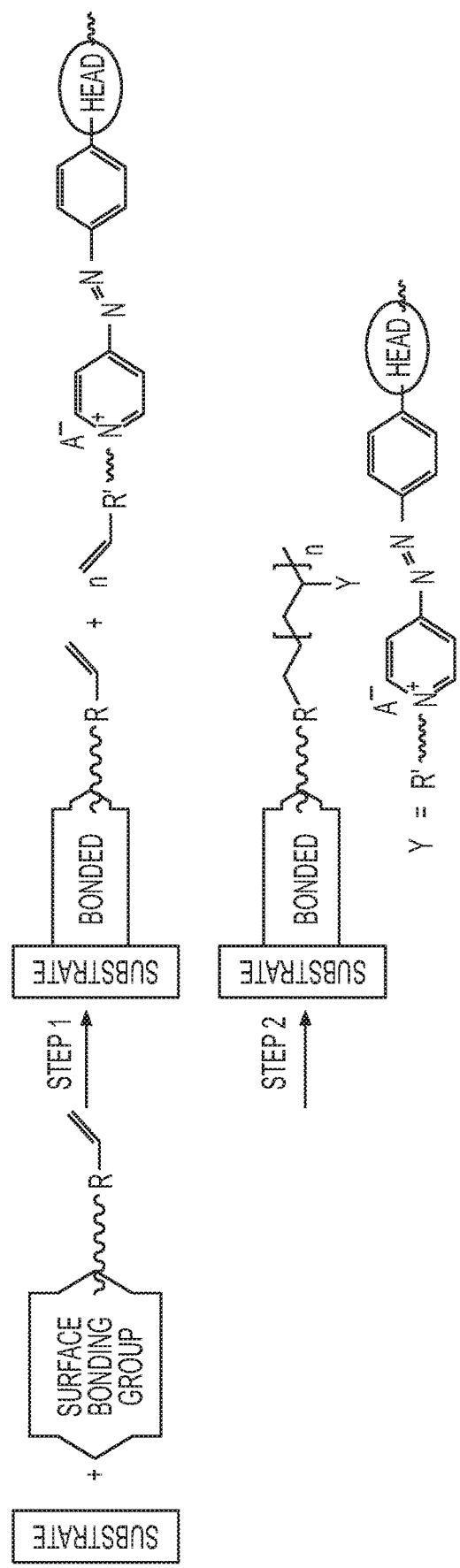
Figure 5B:
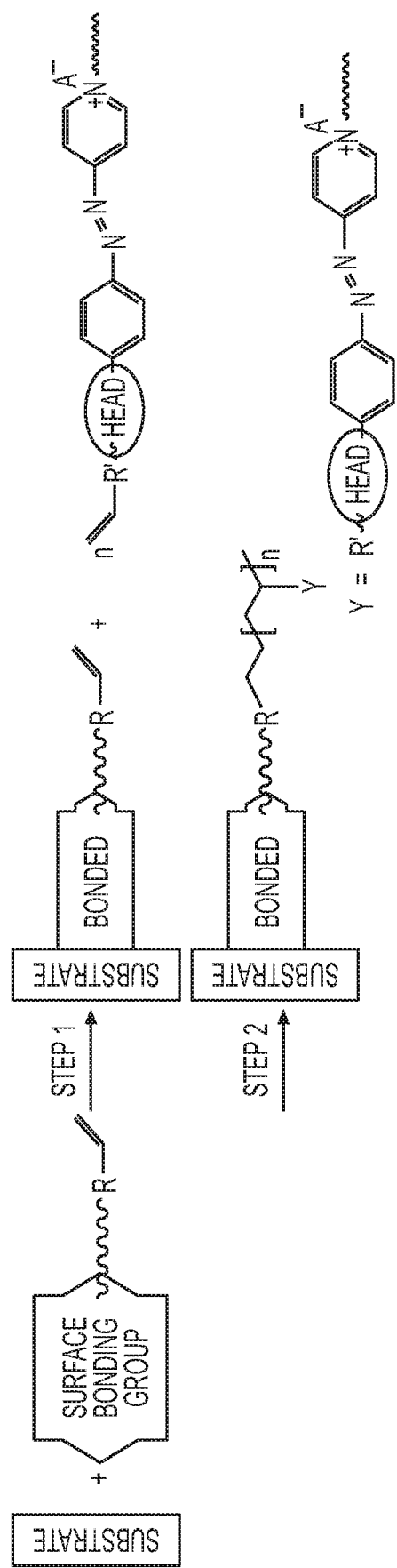

Two-step grafting approaches are shown in FIGS. 5A and 5B. In an embodiment, a first step in the two-step grafting approaches was to functionalize a surface with polymerizable moieties, e.g.,

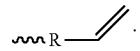

In a second step, the monomers copolymerized with Azo-QPS compounds containing a polymerizable surface bonding group

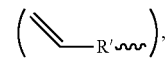

e.g., methacrylate in E)-4-((4-(isobutyryloxy)phenyl)diazenyl)-1-(5-(methacryloyloxy)pentyl)pyridinium bromide. The

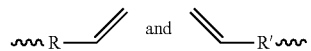

are derivatives of methacrylates, acrylates, vinyl benzyl ether and other vinyl-containing functional groups. These two-step grafting approaches may attach a number (n) of Azo-QPS compounds either from the pyridinium side (example 7, FIG. 5A) or from the Head side (example 8, FIG. 5B) in one step.

Examples 9-10: Three-Step Grafting

Figure 6A:
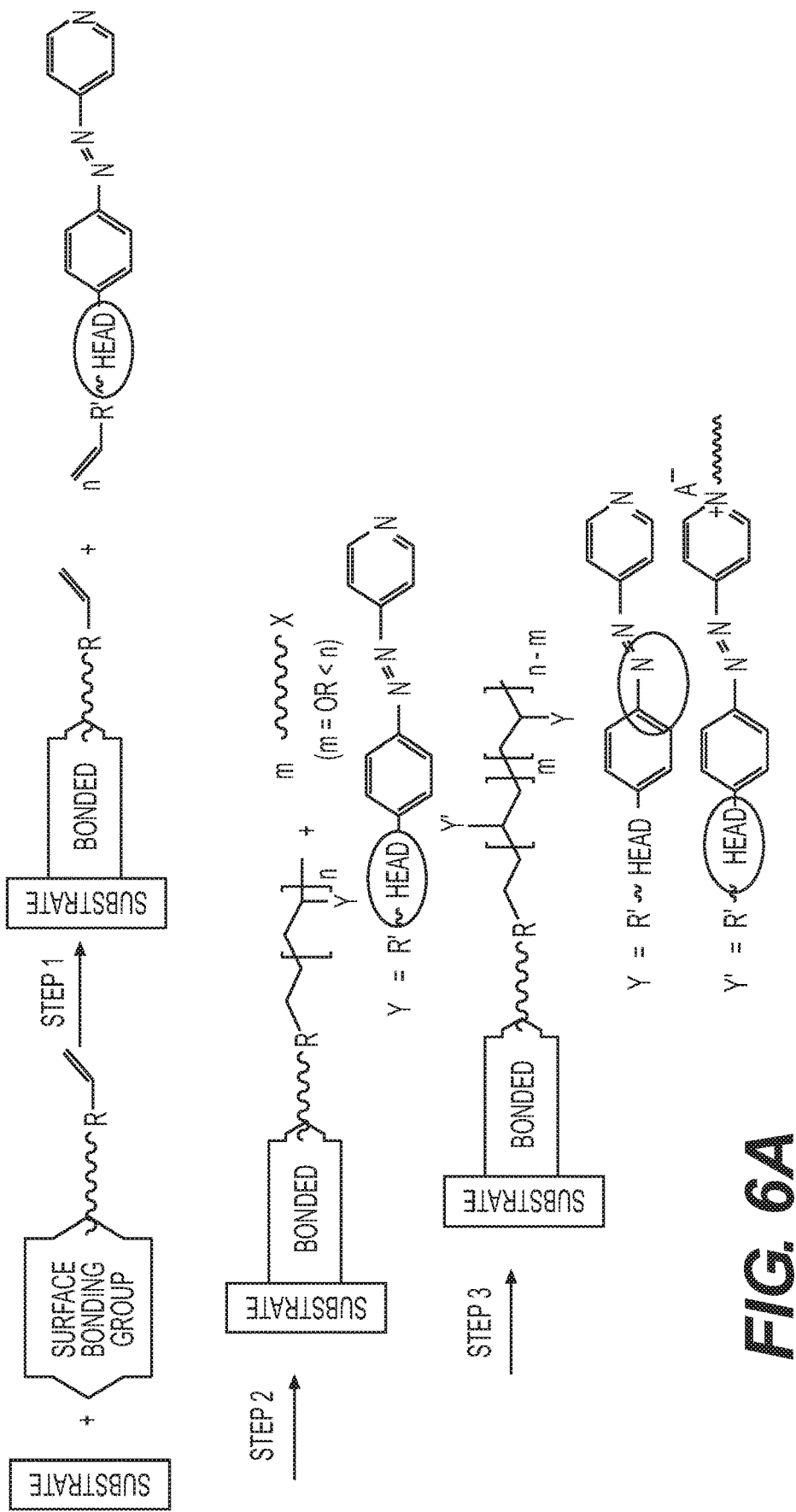
Figure 6B:
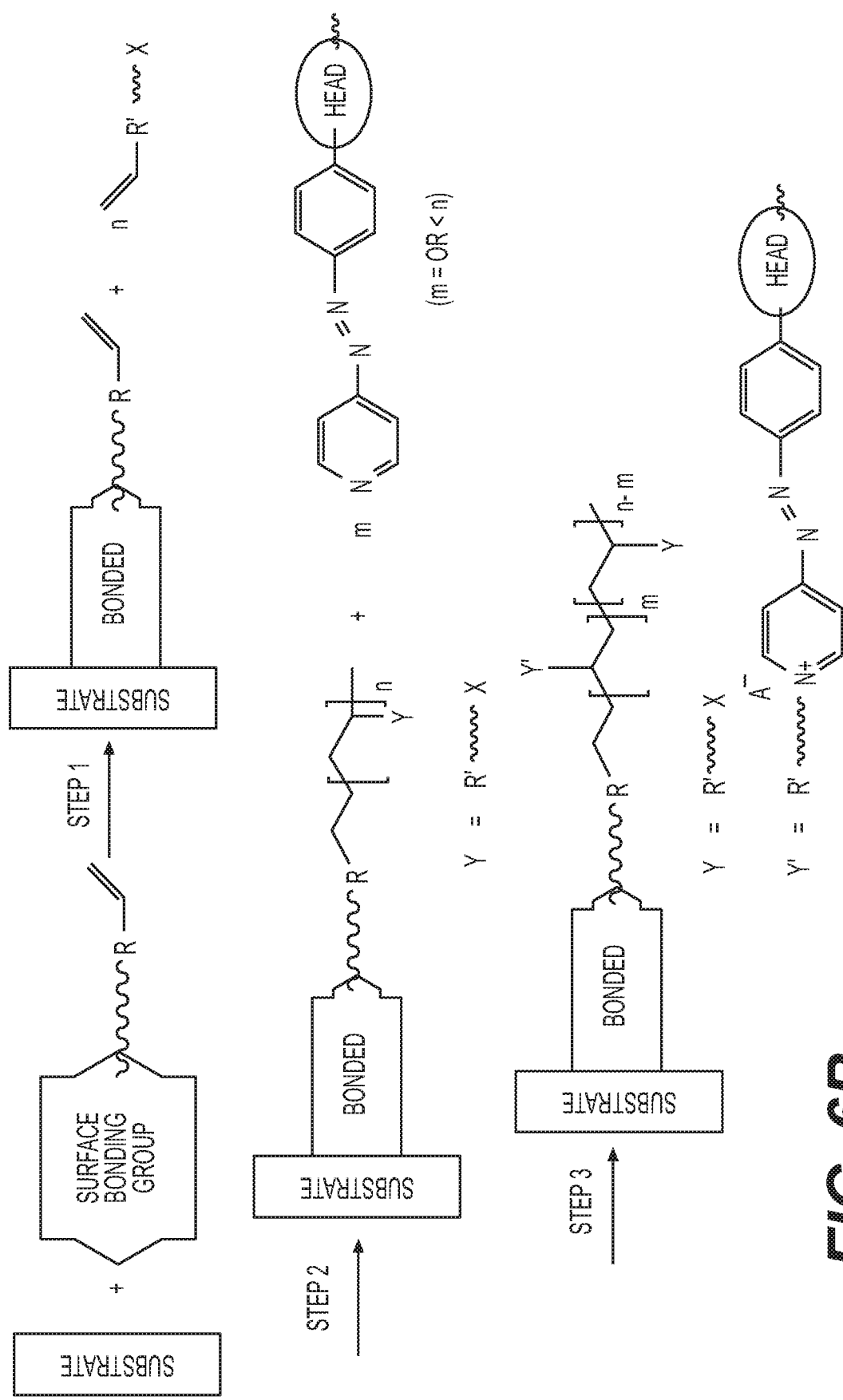

Three-step approaches are shown in FIGS. 6A and 6B. The first steps of these example three-step grafting approaches are the same as those in the two-step grafting approaches of FIGS. 5A and 5B. However, the example three-step grafting approaches then take two steps to graft pyridinium salts on to the substrates. Based on which side is attached first, the three-step grafting approaches are divided into two groups: 1) example 9, grafting from the Head side, and 2) example 10, grafting from spacer to pyridinium salt.

Example 9

When grafting from the Head side, numbers (n) of Azo-pyridine derivatives were copolymerized onto the substrates first through copolymerization of

then numbers (m) of spacers with a functional group (X) reacted with pyridine and formed quaternary pyridinium salts, with m<n due to incompletion of the reactions. When X was a halide, a quaternary pyridinium salt was produced through a Menshutkin reaction; when X was —OH, a quaternary pyridinium salt was produced through a Mitsunobu reaction.

Example 10

When a spacer was grafted on the substrates first, numbers (n) of spacers with a functional group (X) were attached through copolymerization of

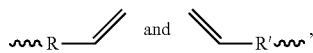

then numbers (m) of Azo-pyridine derivatives reacted with the functional group X and formed quaternary pyridinium salts, with m<n due to incompletion of the reactions. Similar to the above, when X was a halide, a quaternary pyridinium salt was produced through a Menshutkin reaction; when X was —OH, a quaternary pyridinium salt was produced through a Mitsunobu reaction.

Example 11: Copolymerization in Bulk

The Azo-QPS compounds also may copolymerize with methacrylates, acrylates, vinyl benzyl ether and other vinyl-containing functional groups and form pH-sensitive polymers that may be used as substrates or in solutions. These copolymerizations took place between

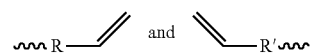

described above with the presence of initiators.

Example 12: Reversible Assembly

The herein disclosed Azo-QPS compounds form pH-sensitive co-assembly with themselves and other compounds with specific chemical functionalities. These compounds interact with Azo-QPS compounds through an acid-base reaction. For example, chlorhexidine ($pK_a$=10.3 and 2.2) acts as a base that reacts with the Azo-QPS-16 ($pK_a$=5.3). Consequently, such interaction triggers the formation of a tightly stacked 7-conjugated systems that capture both in the co-assembly. The co-assembly and disassembly are switchable by varying pH between basic conditions and acidic conditions, or by alternatively adding a base or an acid. Applicants designed the following forms through which the co-assembly occurs: Form 1) on surface using Azo-QPS compounds that are chemically bonded onto a substrate, and Form 2) in solution. The compounds that co-assemble with Azo-QPS compounds possess one or more of the following characteristics: base, Lewis base, organic amine, and pyridine derivatives. Because the interactions in these co-assemblies are specific, pH-sensitive, and instant, the pH-sensitive disassembly may be controlled precisely through varying pH or adding an acid or base; such precise control cannot be achieved by non-specific, physical-absorption-based pH-sensitive mechanisms.

EXAMPLES 13-19: CHARACTERIZATION

Example 13: Acid-Enhanced Antibacterial Efficacy

Azo-QPS-C16 was effective on both Gram-positive *E. coli* and Gram-negative *S. mutans* bacteria. The ability of bacteria to proliferate after exposure to Azo-QPS-C16 was characterized by adding growth medium and measuring the optical density (OD) at 600 nm every 15 minutes in pH 4.1, 5.8, and 7.9 buffer. Exposure to 2.5 µg/mL of Azo-QPS-C16 at pH 4.1 fully inhibited *E. coli* growth up to 19 hours. However, exposure at pH 7.9 required a much higher concentration (40 µg/mL) to inhibit cell growth. Obvious growth of *E. coli* was observed for all buffer control measurements including different pH values with and without dimethyl sulfoxide (DMSO). The pH dependence of bactericidal activity of Azo-QPS-C16 in terms of minimum bactericidal concentration (MBC) was evaluated by inoculating cultures onto a Lysogeny Broth (LB) agar plate after treating the cells with a twofold dilution series of Azo-QPS-C16. As pH increased, the MBC correspondingly increased. A 16-fold difference in MBC was observed between pH 4.1 and pH 7.9. The results are shown in Table 1, below.

TABLE 1

| | MBC (µg/mL) | |
|---|---|---|
| pH value | *E. coli* | *S. mutans* |
| 4.1 | 2.5 | 1.25 |
| 5.8 | 10 | 5 |
| 7.9 | 40 | 10 |

As can be seen in Table 1, applicants observed similar pH-sensitive antibacterial activity of Azo-QPS-C16 towards the Gram-positive, lactic acid producing, cariogenic bacteria *S. mutans*. Specifically, MBC assessments show that Azo-QPS-C16 is 8-fold more effective against *S. mutans* in acidic conditions compared to mildly basic conditions.

Bacterial strains and growth conditions. *Streptococcus mutans* (*S. mutans*, UA159) and *Escherichia coli* (*E. coli*, K12) were purchased from ATCC (American Type Culture Collection, Manassas, Va., USA). Todd Hewitt Broth (THB), and Lysogeny Broth (LB) powder and agar were purchased from BD (Becton, Dickinson and Company, Franklin Lakes, N.J., USA). Planktonic cultures were inoculated from 25% (by volume) glycerol frozen stocks stored at −80° C. *E. coli* cultures were grown in LB at 37° C. in a shaker-incubator. *S. mutans* cultures were grown in THB at 37° C. with 5% (by volume) $CO_2$ overnight.

Bacterial growth curves. Overnight cultures of *E. coli* and *S. mutans* were diluted directly into buffers with different pH values (100 mmol/L, pH 4.1 sodium acetate buffer, pH 5.8 sodium phosphate buffer, and pH 7.9 sodium phosphate buffer) to an optical density at 600 nm (OD600) of approximately 0.001.

In a 96-well plate, 2 µL of Azo-QPS-C16 at various concentrations in dimethyl sulfoxide (DMSO) were added to 98 µL of bacteria suspension per well for a final concentration ranging from a 2-fold dilution series between 40 to 1.25 µg/mL of Azo-QPS-C16. After 45 minutes of treatment at room temperature, 10 µL from each well was transferred to a new 96-well plate already containing 100 µL growth media per well to measure the growth curves. $E.\ coli$ were cultured at 37° C., and the OD600 of each well was measured by a Tecan Spark microplate reader (Männedorf, Switzerland) every 15 minutes for up to 19 hours, with 30 seconds shaking before each measurement. $S.\ mutans$ were grown at 37° C. with 5% CO2, and the OD600 of each well was measured periodically using a Molecular Devices (Sunnyvale, Calif.) SpectraMax M5 microplate reader. All experiments were conducted in triplicate and repeated at least three times on different days.

Minimum bactericidal concentration (MBC) determination. MBC values were determined by agar colony formation. The same treatment was applied to the bacteria as for the growth curve measurement. 5 µL of the suspended cells from each well were spotted onto an agar plate and incubated for 48 hours to allow colony formation, and the presence or absence of bacterial growth was determined by naked eye. All experiments were conducted in triplicate and repeated at least three times on different days.

Example 14: pH-Sensitive Physicochemical Properties

Azo-QPS-C16 exhibits pH-sensitive physicochemical properties that correlate with the acid-enhanced antibacterial activity of Azo-QPS-16. Aqueous solutions of 0.01 mmol/L (5.7 µg/mL) Azo-QPS-C16 ( ) appear clear orange and purple in acidic and basic conditions, respectively, consistent with the red-shift observed in UV-Vis spectra. UV-Vis spectra were recorded on a Thermo Spectronic Genesys 5 UV-Vis spectrophotometer (Thermo Scientific, Waltham, Mass. USA) using quartz cuvettes with 1 cm path length at 298 K after baseline correction. Intensification of a peak centered at 554 nm and simultaneous decrease of a peak at 347 nm are proportional to a change in pH from 4.1 to 7.9. Similar absorbance peaks were detected for 0.05 mmol/L, (28.6 µg/mL) Azo-QPS-C16 in DMSO, where molar equivalents of base, e.g., triethylamine (TEA) were added; the decrease of peak intensity at 347 nm is proportional to an increasing mole ratio of TEA to QPS.

Example 15. Acid-/Base-Induced Switchable Assembly

In addition to color changes (e.g., orange to purple), assembly of Azo-QPS-C16 at various pH values was observed with dynamic light scattering (DLS). Particles with an average hydrodynamic diameter of 51±19 nm formed in mildly basic conditions, occurring simultaneously with the appearance of the absorbance peak at 554 nm. No particles were found in pH 4.1 buffer. Reversible switching between acidic and basic conditions in DMSO was demonstrated over three cycles through successive additions of 5 molar equivalents TEA and then trifluoroacetic acid (TFA). One cycle corresponds to the addition of a base and an acid. In base and acid, respectively, the absorbance at 554 nm increased and then decreased, and the particles formed and disassembled.

The short chain Azo-QPS-C2 showed similar switchable assembly in terms of appearance and particle size distribution. The UV-Vis spectra of Azo-QPS-C2 had two peaks at 350 nm and 540 nm, compared to 347 nm and 554 nm in the spectra of Azo-QPS-C16. DLS determined that these two compounds Azo-QPS-C2 and Azo-QPS-C16 had the same hydrodynamic diameter and particle size distribution when a base was added. This observation indicates that the chain length of the tails has minimal effect on the assembly of these two Azo compounds.

Dynamic light scattering (DLS) was performed using a Nicomp 380 ZLS DLS system (Particle Sizing Systems Inc., Santa Barbara, Calif.). Samples were contained in disposable glass culture tubes. Prior to sample loading, the tubes were blown with nitrogen gas and filled with 0.4 mL of a dye sample. The tubes were sealed using parafilm and then centrifuged at 14,000 rpm (19,000 g) for 5 minutes to separate larger particles. Samples were placed in the instrument and allowed to attain thermal equilibrium. An autocorrelation function was acquired for 3 minutes at 173° scattering angle. A Laplace inversion-based Nicomp routine was used to find the distribution of decay rates. The decay rates are linked to the effective sphere hydrodynamic diameters by the appropriate equations. The size distribution is reported as a discrete set of diameter bins and corresponding intensity weighted fractions as probabilities assigned to diameter bins.

Example 16: Electrochemical Properties of Azo-QPS Compounds

Cyclic voltammetry (CV) was used to evaluate the electrochemical properties of the Azo-QPS compounds in solution, adsorbed on glassy carbon, and covalently bonded to glassy carbon in a typical three electrode configuration. The working electrode was a 3 mm diameter glassy carbon disk (0.28 cm$^2$) polished with 1 µm alumina and then rinsed with copious amounts of water. The cell was a 20-mL glass vial with a platinum auxiliary electrode and an Ag|AgCl|1 mol/L KCl reference electrode (called Ag/AgCl) in a 3% agar+0.2 mol/L KNO$_3$ salt bridge. Before use, glassware was immersed in 3 mol/L HNO$_3$ overnight and then rinsing with copious amounts of water. CV was performed using the potentiostat of a Model 920D Scanning Electrochemical Microscope System (CH Instruments, Austin, Tex.) or a Model SP-300 potentiostat (Bio-Logic, Knoxville, Tenn.).

Figure 7A:
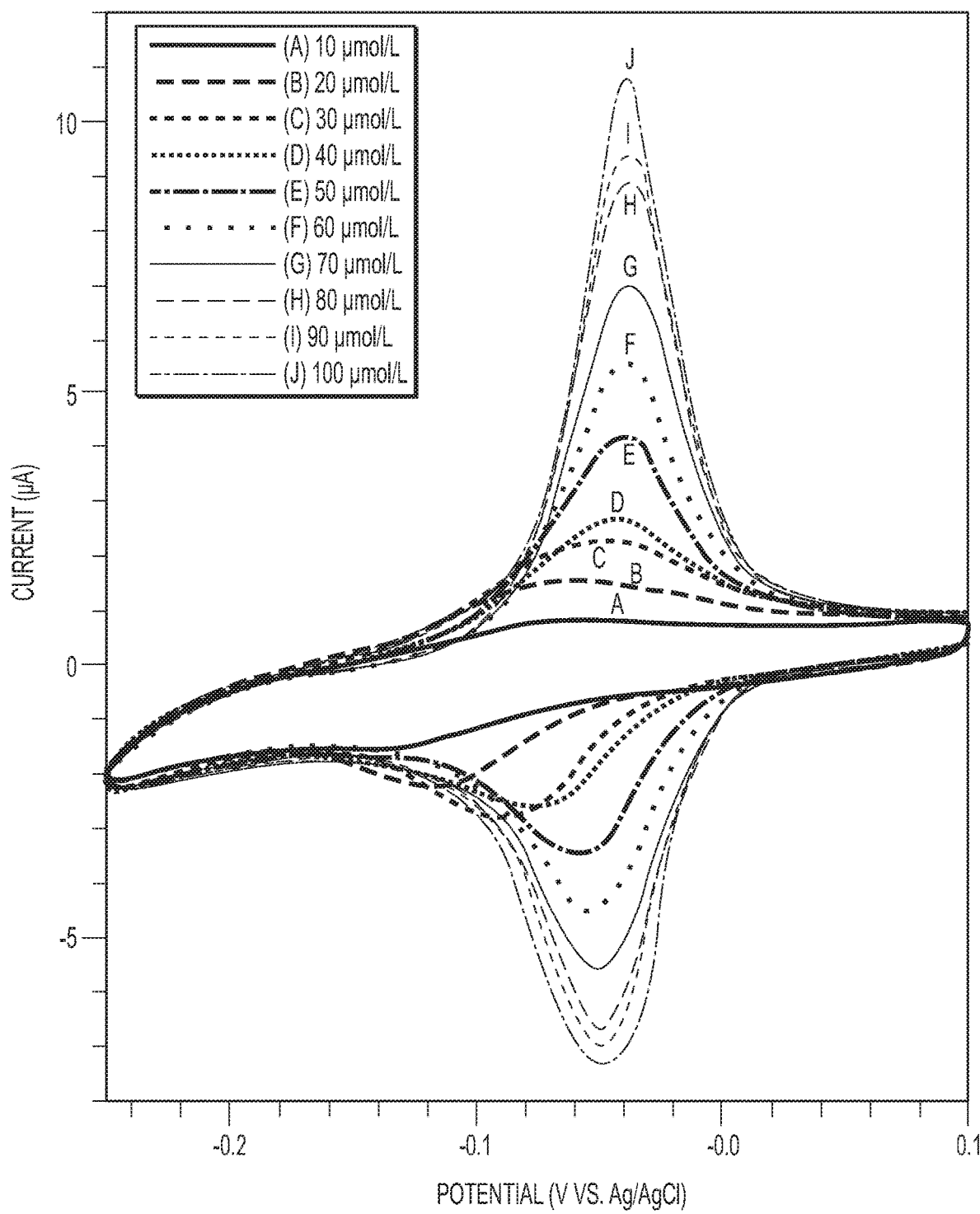
FIGS. 7A-7D illustrate example cyclic voltammograms (CVs) of the herein disclosed Azo-QPS-16 compound.

Aliquots containing 10 µL of 1 mmol/L (572 µg/mL) Azo-QPS-C16 in DMSO were added to 10 mL of 0.1 mol/L phosphate buffer, pH 6.8, to evaluate the CV behavior as a function of Azo-QPS-C16 concentration in solution with a sweep rate, v, of 20 mV/s (FIG. 7A). As the concentration of Azo-QPS-C16 increased, the peak current for in the reduction and oxidation waves increased, and the average peak potential, $E_{1/2}$, of the reduction and oxidation waves shifted positive from −0.10 V to −0.05 V vs. Ag/AgCl. The observed reduction current likely arises from the reduction of the azobenzene group in the pH-core 10 to hydrazobenzene (reduced Azo-QPS-C16), and the oxidation current is due to the oxidation of the hydrazobenzene back to azobenzene. The reduction and oxidation waves became narrower at concentrations above 40 µmol/L (23 µg/mL) and the difference in the peak potentials, ΔE, decreased, suggesting that the Azo-QPS-C16 adsorbed to the glassy carbon at concentrations between 50 µmol/L (29 µg/mL) and 100 µmol/L (57

μg/mL) of Azo-QPS-C16. The ratio of the oxidation peak current, $i_{pa}$, to the reduction peak current, $i_pc$, was greater than unity for concentrations above 40 μmol/L, indicating that Azo-QPS-C16 weakly adsorbed to glassy carbon below 40 μmol/L and then reduced Azo-QPS-C16 adsorbed at concentrations higher than 40 μmol/L.

Figure 7B:
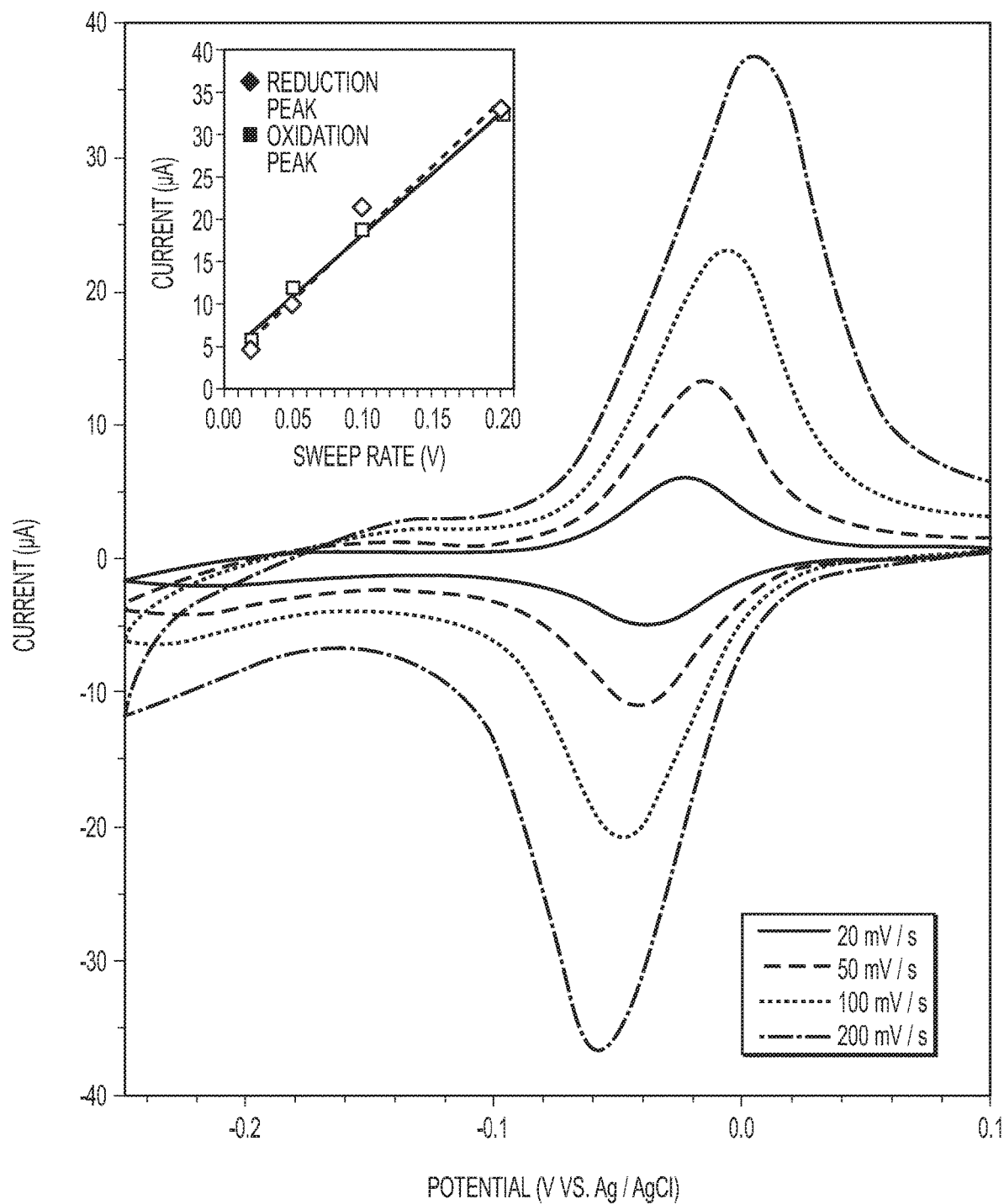

To examine the electrochemical properties of surface adsorbed Azo-QPS compounds, a glassy carbon electrode with a film of Azo-QPS-C16 adsorbed from 100 μmol/L Azo-QPS-C16 in a DMSO/phosphate buffer was immersed in 0.1 mol/L phosphate buffer, pH 6.8. During the CV, a redox couple with an $E_{1/2}$ of −0.05 mV vs. Ag/AgCl, similar to the CVs with Azo-QPS-C16 in solution (FIG. 7B). Plots of $i_{pc}$ vs. v and $i_{pa}$ vs. v and were linear ($i_{pc}$=146 v+4 and $i_{pa}$=158 v+3), confirming that the Azo-QPS-C16 absorbs to glassy carbon (inset of FIG. 7B). CV at varying sweep rates was also performed on films of Azo-QPS-C16 compound adsorbed from solutions of the compound in DMSO and isopropanol.

The surface coverage, Γ (in mol/cm$^2$), of a reversible, electroactive compound immobilized on an electrode can be determined from the equation $i_p=(n^2F^2vA\Gamma)/(4RT)$, where $i_p$ is the peak current in amperes (A), n is one electron, F is Faraday's constant (96,485 C/mol), v is sweep rate in V/s, A is the electrode area in cm$^2$, R is the molar gas constant (8.314 J/mol/K), and T is the temperature in K. The estimated surface coverage of Azo-QPS-C16 formed from the DMSO/buffer system was 200 μmol/cm$^2$. The surface coverage of the films formed in a DMSO/buffer was larger than that in DMSO (60 μmol/cm$^2$) and in isopropanol (30 μmol/cm$^2$), suggesting that the interaction between the Azo-QPS compound and the glassy carbon substrate is hydrophobic in nature. The long alkyl chain in the Azo-QPS-16 compound may promote the hydrophobic interaction.

Figure 7C:
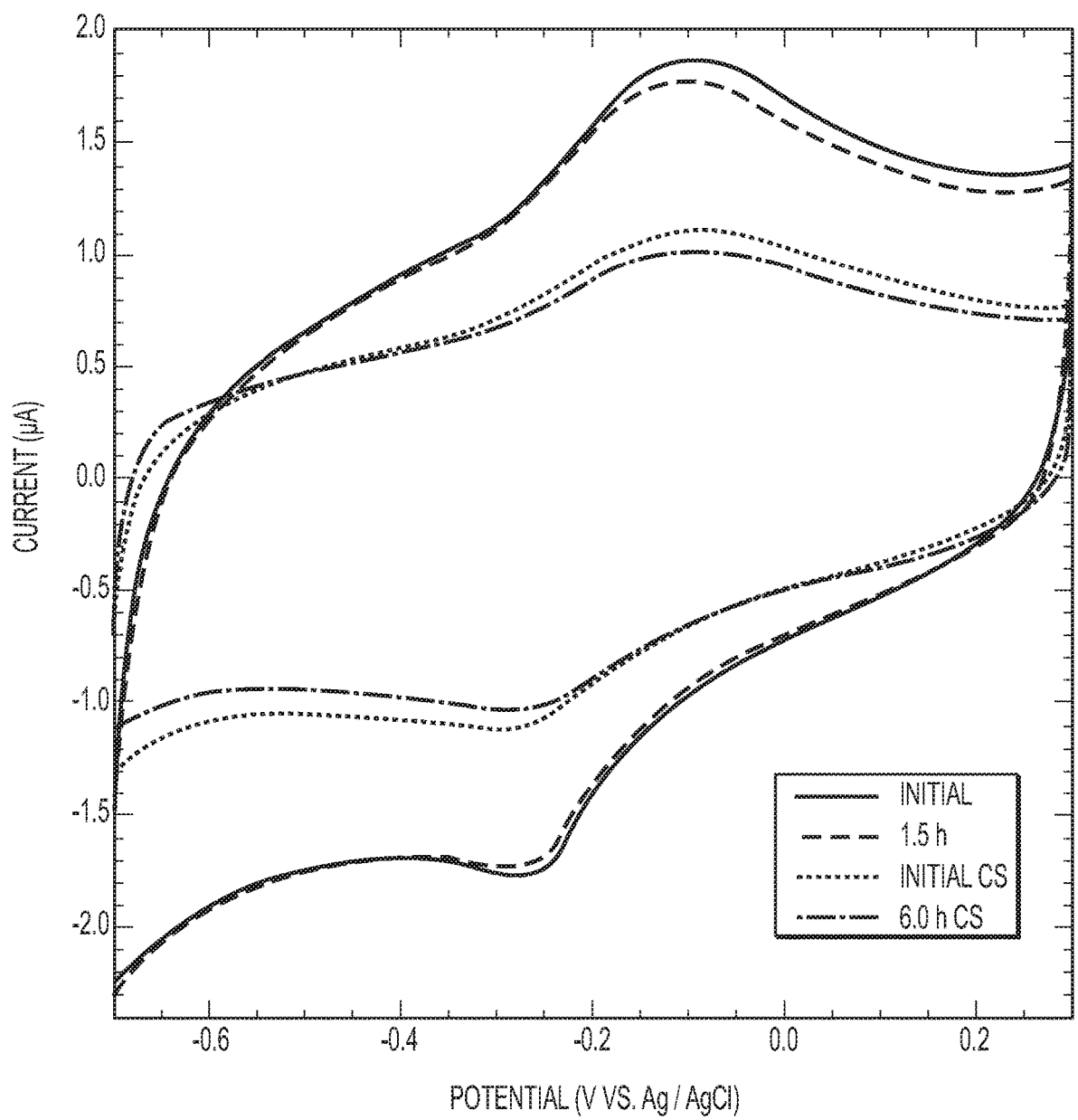

The surface coverage of the surface adsorbed Azo-QPS-C16 decreased to 75% of the original value after 45 minutes of immersion for 45 minutes in the buffer solution, indicating that the film readily desorbs in the buffer solution. Therefore, the applicants pursued methods to improve the signal stability by covalently bonding the Azo-QPS to the substrate. When the Azo-QPS compound was covalently bonded using silanization, the surface coverage of the compound was 92% of the original value (40 μmol/cm$^2$) after 1.5 hours in phosphate buffered saline (PBS), pH 7.4, using a sweep rate of 50 mV/s (FIG. 7C). In addition, when a film of chitosan (CS) was formed by drop casting and drying a chitosan solution on the covalently bonded Azo-QPS, the signal decreased by 46% of the original, bare film but then was near 100% after 6 hours in the phosphate buffer (FIG. 7C).

Figure 7D:
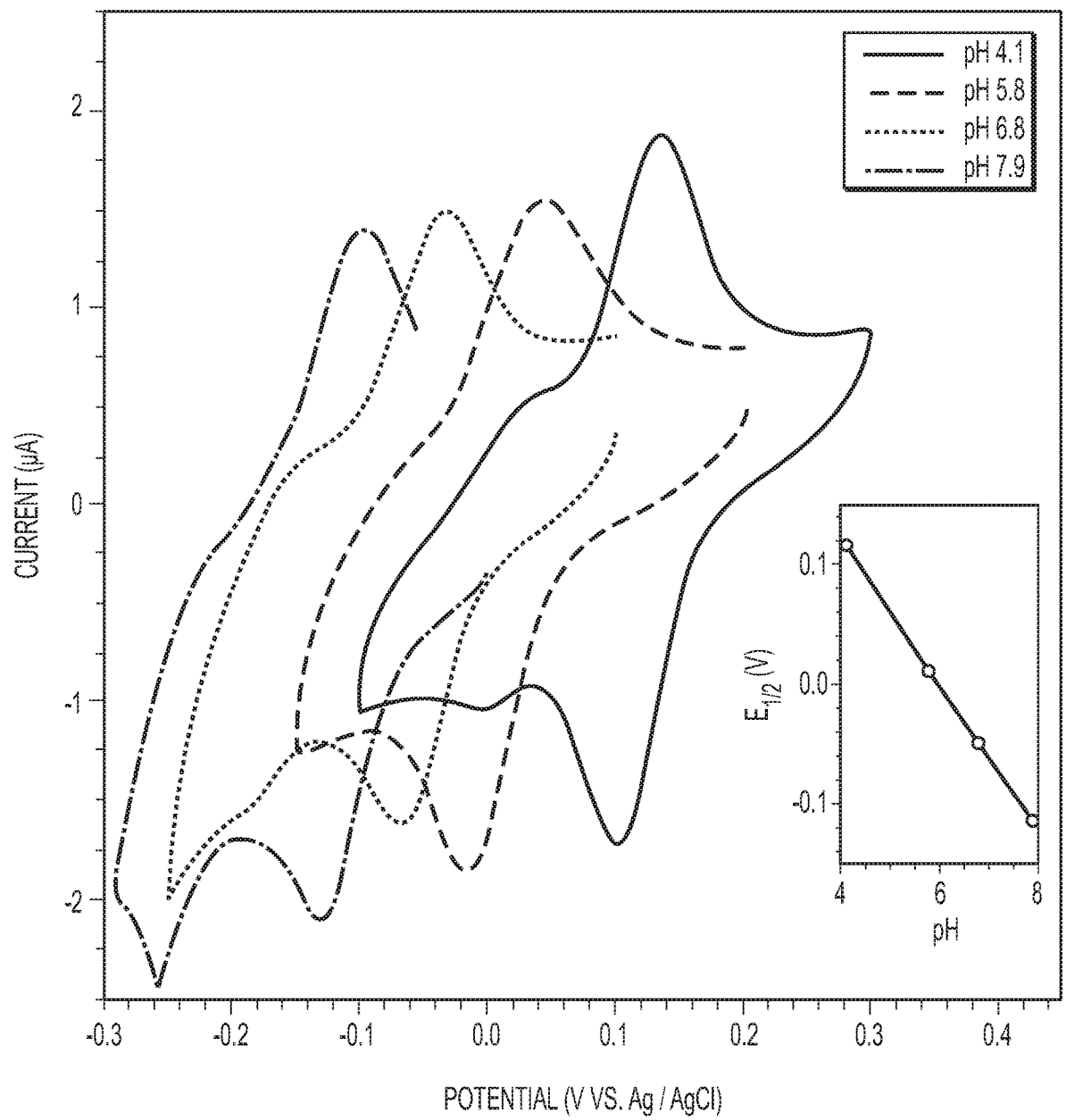

The effect of pH on electrochemical potential of the Azo-QPS compound was examined by CV to understand the role of protonation/deprotonation in Azo-QPS and to test the sensitivity of the compound to changes in pH. The glassy carbon with a film of surface adsorbed Azo-QPS-C16 was immersed in buffer solutions at varying pH values, and then CV was performed (FIG. 7D). Plotting $E_{1/2}$, vs. pH revealed a slope of −61 mV/pH unit between pH values of 4.1 and 7.9, indicating that the Azo-QPS is sensitive to pH and undergoes a one proton per electron transfer process of FIG. 7D.

Example 17. Label-Free Electrochemical Methods for Different Biomarkers

A highly sensitive electrochemical (HSEC) assay quantification of cardiac troponins (cTns) is based on changes in the electrochemical redox response of Azo-QPS due to the interaction of cTnT and anti-cTnT antibody. TnT is a tropomyosin-binding subunit that regulates the interaction of troponin complex with thin filaments. The response was evaluated through electroanalytical methods: cyclic voltammetry (CV) and square wave voltammetry (SWV). The level of cTnT is reflected by the change of peak current of substrates functionalized with Azo-QPS. Specifically, the working electrode was coated with Azo-QPS, monoclonal antibody of cTnT for specific binding, and other sensitivity enhancing components including metal nanoparticles and chitosan. High concentrations of cTnT increased the amount of protein attached on the electrode through antigen-antibody interaction, hence decreasing the electron transfer and peak current. The change in peak current was proportional to the concentration of cTnT in solution. The mathematic correlation was defined by the antigen-antibody interaction, the design of the biosensor, and the experiment parameters. A calibration cure was established to determine the concentration of cTnT in both PBS and pooled human saliva. This HSEC assay is a label-free process and requires no treatment of the specimen. Through selection of antibody and implementing the corresponding calibration curves, the HSEC assay may be used in quantification of other biomarkers such as cardiac troponin I (inhibitory, cTnI) and other antigens.

Example 18: Chemistry of Assembly in Solutions

The chemistry revealed by NMR spectra confirms the key role of the phenyl-azo-pyridinium core in the assembly of Azo-QPS-C16/2. In addition, NMR spectra suggest that there are interactions between these Azo-QPS compounds and the TEA base. The spectrum of the solution differs in a number of ways from that of the components. First, the peaks of protons on the aromatic rings and the first carbon of the QPS's Tail yielded very broad resonance signals; second, the protons on TEA were unobservable; third, no peak shift or change in integration were identified in the peaks of the other protons; and finally, no new peaks appeared. Peak broadening and unobservable protons are likely due to assembly, which has been reported in supramolecular gels formed by low molecular weight species and agrees well with the particle formation determined by DLS. The assembly significantly increases the correlation time, consequently, leads to a very short transversal relaxation time, and very broad or unobservable signals. Moreover, the lack of TEA protons suggests that participates in the assembly. TEA is a base and may interact with the Azo-QPS-C16 which is weakly acidic, $pK_a$=5.33. The product of this interaction may be a chemical complex formed by the base and the Azo-QPS-C16. Based on the above-described NMR results combined with the base-induced red-shift in UV-Vis spectra and assembly determined by DLS, the applicants believe that the interaction of TEA with Azo-QPS-C16 triggers assembly of tightly stacked 7-conjugated cores, formed by two or more Azo-QPS-C16 molecules and the base.

Applicants developed a new model to predict molecular assembly. This model uses a sandwich stacking configuration where the cores of the trans-isomer of Azo-QPS-C16 molecules are aligned in parallel. As applicants further postulate, as shown in FIG. 1, the assembled Azo-QPS-C16 molecules 2 are packed with an alternating head-to-tail arrangement that minimizes the potential repulsion among the QPS compounds due to the positive charge of the pyridinium salt. This stacking model also maximizes the participation of TEA since the interaction of TEA with the Azo-QPS-C16 is most likely taking place close to the QPS compounds. The broadening resonance signals at 4.69 ppm in d-DMSO (5.11 ppm in CDCl3), which belong to the protons on the first carbon of the pyridinium tail, strongly suggest such a possibility. As a result of charge repulsion and potential steric hindrance, head-to-tail arrangement is more favored than head-to-head or tail-to-tail arrangements and is likely to create the most impenetrable packing of the phenyl-azo-pyridinium core. Furthermore, the interaction of TEA with Azo-QPS-C16 molecules also may serve as a shutter to the access of the already tightly stacked core, thus isolating the core of the assembled Azo-QPS-16C molecules from their heads and tails.

Example 19: Correlated but Different Mechanism for pH-Sensitivity and Acid-Enhanced Antibacterial Efficacy The above results demonstrate that Azo-QPS-C16 is multifunctional and pH-sensitive in both solutions and adsorbed films. In solution, the pH-sensitivity is triggered by acid-base interaction and leads to different assembly stages of tightly stacked π-conjugated phenyl-azo-pyridinium core and base. The participation of base moieties may be $OH^-$ ion or hydroxyl-containing derivatives in aqueous solutions or moisture-containing solvents. In adsorbed films, the pH-sensitivity is due to the redox couple that likely arises from the reduction of azobenzene to hydrazobenzene and vice versa. In both states, the pH sensitivity is closely interrelated to the chemistry of the phenyl-azo-pyridinium core. The chain length of the QPS tail has minimal impact on the pH-sensitivity in solutions. However, the long carbon chain is vital to the acid-enhanced antibacterial efficacy, which is determined by a combination of multiple factors including the amphiphilic properties, cations, charge density and counter ions. In acidic conditions, the MBC of Azo-QPS-C16 for *E. coli* and *S. mutans* was 2.5 μg/mL and 1.25 μg/mL, respectively. In comparison, the short chain analog Azo-QPS-C2 did not inhibit bacterial growth even at a concentration that was 400 to 800 times higher. Such distinct differences in antibacterial efficacy corresponding to the chain length not only validate the importance of the long-chain carbon tail in providing the needed amphiphilic properties of a strong antibacterial QPS, these differences also offer a tool to design and prepare pH-sensitive materials with a broad range of antibacterial efficacy. Moreover, in mildly basic conditions, Azo-QPS-C16 molecules interact with the base to form nanoparticles with an average hydrodynamic diameter of 51±19 nm containing tens of Azo-QPS-C16 molecules. Assuming each Azo-QPS-C16 molecule and one particle as an individual effective antibacterial site, adjusting the pH changes the number of free molecules and assemblies, which controls the number of effective sites and thus the antibacterial activity.

We claim:

1. A multi-functional, stimuli-responsive material, comprising:
   a substrate functionalized with a pH-sensitive Azo-QPS compound; and
   the Azo-QPS compound, comprising:
       a positively-charged phenyl-azo-pyridinium core,
       an anion affiliated with the core,
       a head group consisting of a compound selected from one of a first group consisting of —OH, —NH$_2$, —NMe$_2$, —C$_n$H$_{(2n+1)}$, —C$_n$H$_{(2n-1)}$, —OCH$_3$, OC$_2$H$_5$, and their derivatives, and a second group consisting of methacrylate, acrylate, styrene, vinyl benzyl, and their derivatives,
       a tail group consisting of a compound selected from a group consisting of —C$_n$H$_{(2n+1)}$, —C$_n$H$_{(2n-1)}$, and their derivatives,
       wherein n is an integer between 2 and 20,
       a surface bonding group coupling the pH-sensitive Azo-QPS compound to the substrate, and
       a spacer connecting the pH-sensitive Azo-QPS compound to the surface bonding group.

2. The multi-functional, stimuli-responsive material of claim 1, wherein the anion is selected from a group consisting of $NO_3^-$, $NO_2^-$, $SCN^-$, $CN^-$, $PO_4^{3-}$, $SO_4^{2-}$, $SO_4^{2-}$, $F^-$, $Cl^-$, $Br^-$, $I^-$, $BF_4^-$, $PF_6^-$, $AsF_6^-$, $SbF_6^-$, $CH_3CO_2^-$, $CF_3SO_3^-$, $(CF_3SO_2)_2N^-$, $(CF_3SO_2)_3C^-$, and $CF_3COO^-$.

3. The multi-functional, stimuli-responsive material of claim 1, wherein the surface bonding group chemically bonds the pH-sensitive Azo-QPS compound to the substrate through chemical reactions comprising polymerization, silanization, and thiolation, and crosslinking with aryl diazonium, carbodiimide, or cyanuric chloride functional groups.

4. The multi-functional, stimuli-responsive material of claim 1, wherein the head group is covalently bonded to the phenyl-azo-pyridinium core from a phenyl side through one of C—C and C—O bonding, wherein, the C—O bonding is in a form of ether or ester functional groups.

5. The multi-functional, stimuli-responsive material of claim 1, wherein the spacer is 0 to 16 members chosen from a group consisting of an alkyl chain and an alkoxyl chain, and wherein the spacer is attached to a nitrogen of a pyridinium ring.

6. The multi-functional, stimuli-responsive material, wherein the substrate of claim 1 is chosen from a group of materials consisting of conductive materials, semiconductor materials, and nonconductive materials,
   wherein the conductor and semiconductor materials are chosen from a group consisting of:
       carbon materials, wherein the carbon materials are chosen from a group consisting of glassy carbon, graphite, graphene, carbon nanotubes, and amorphous carbon,
       metals, wherein the metals are chosen from a group consisting of gold, platinum, and silver,
       silicon,
       metal oxides selected from a group consisting of indium tin oxide (ITO) and tin oxide, and
       conductive organic polymers selected from a group consisting of polyaniline, polypyrrole, polythiophene, and poly(vinylferrocene);
   wherein the nonconductive materials are chosen from a group consisting of:
       polymers chosen from a group consisting of polyester and vinyl ester resins,
       glass,
       metal oxides, and
       silicon.

7. The multi-functional, stimuli-responsive material of claim 1, wherein the substrate comprises a surface of a material in a form selected from a group consisting of films, particles, nanoparticles, particles with porous structures, mesoporous particles, and membranes.

8. The multi-functional, stimuli-responsive material of claim 1, wherein the substrate is used for applications comprising drug delivery, biosensor, immunosensor, targeted treatment, antimicrobial material, anti-fouling material, pH indicator, and pH sensor.

9. A co-assembly of pH-sensitive Azo-QPS compounds with chemically selected compounds that form suspensions in solutions, wherein the pH-sensitive Azo-QPS compounds comprise:
- a positively-charged phenyl-azo-pyridinium core;
- an anion affiliated with the core;
- a head group consisting of a compound selected from one of a first group consisting of —OH, —NH$_2$, —NMe$_2$, —C$_n$H$_{(2n+1)}$, —C$_n$H$_{(2n-1)}$, —OCH$_3$, OC$_2$H$_5$, and their derivatives, and a second group consisting of methacrylate, acrylate, styrene, vinyl benzyl, and their derivatives;
- a tail group consisting of a compound selected from a group consisting of —C$_n$H$_{(2n+1)}$, —C$_n$H$_{(2n-1)}$, and their derivatives, wherein n is an integer between 2 and 20; and
- a spacer attached to the N atom on the Azo-QPS compound.

10. The co-assembly of pH-sensitive Azo-QPS compounds of claim 9, wherein the anion is selected from a group consisting of NO$_3^-$, NO$_2^-$, SCN$^-$, CN$^-$, PO$_4^{3-}$, SO$_4^{2-}$, SO$_4^{2-}$, F$^-$, Cl$^-$, Br$^-$, I$^-$, BF$_4^-$, PF$_6^-$, AsF$_6^-$, SbF$_6^-$, CH$_3$CO$_2^-$, CF$_3$SO$_3^-$, (CF$_3$SO$_2$)$_2$N$^-$, (CF$_3$SO$_2$)$_3$C$^-$, and CF$_3$COO$^-$.

11. The co-assembly of pH-sensitive Azo-QPS compounds of claim 9, wherein the head group is covalently bonded to the phenyl-azo-pyridinium core from a phenyl side through one of C—C and C—O bonding, wherein, the C—O bonding is in a form of one of ether functional groups and ester functional groups.

12. The co-assembly of pH-sensitive Azo-QPS compounds of claim 9, wherein the spacer is 0 to 16 members chosen from a group consisting of an alkyl chain and an alkoxyl chain, and wherein the spacer is attached to a nitrogen of a pyridinium ring.

13. The co-assembly of pH-sensitive Azo-QPS compounds of claim 9 chosen from a group of compounds comprising primary amine, secondary amine, tertiary amine, methylene blue, and Lewis base.

14. The co-assembly pH sensitive Azo-QPS compounds of claim 13, wherein a pH sensitive Azo-QPS compound is bonded to a substrate and the pH sensitive Azo-QPS compound bonded to the substrate is used for applications comprising drug delivery, targeted treatment, antimicrobial material, anti-fouling material, pH indicator, and pH sensor.

15. The co-assembly of pH sensitive Azo-QPS compounds of claim 14, wherein the substrate chosen from a group of materials consisting of conductive materials, semiconductor materials, and nonconductive materials.

16. A co-assembly of a pH sensitive Azo-QPS compound bonded to the substrate of claim 15 used for applications comprising biosensor, immunosensor, and a stimuli-responsive device.

* * * * *

UNITED STATES PATENT AND TRADEMARK OFFICE
CERTIFICATE OF CORRECTION

PATENT NO.         : 11,104,647 B2
APPLICATION NO.    : 16/545110
DATED              : August 31, 2021
INVENTOR(S)        : Jirun Sun et al.

Page 1 of 1

It is certified that error appears in the above-identified patent and that said Letters Patent is hereby corrected as shown below:

In the Specification

The following should replace the paragraph at Column 1, Lines 22-25:
STATEMENT OF FEDERALLY SPONSORED RESEARCH
This invention was made with government support under grants DE023752 awarded by the National Institutes of Health. The government has certain rights in the invention.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*